US007070941B2

(12) United States Patent
Zhao et al.

(10) Patent No.: US 7,070,941 B2
(45) Date of Patent: Jul. 4, 2006

(54) METHODS AND COMPOSITIONS FOR TAGGING VIA AZIDO SUBSTRATES

(75) Inventors: Yingming Zhao, Dallas, TX (US); John R. Falck, University Park, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 22 days.

(21) Appl. No.: 10/715,329

(22) Filed: Nov. 17, 2003

(65) Prior Publication Data

US 2005/0106627 A1    May 19, 2005

(51) Int. Cl.
G01N 33/53        (2006.01)
(52) U.S. Cl. .................. 435/7.1; 435/7.2; 435/7.4; 435/7.5; 435/7.6; 435/7.7; 435/7.71; 435/7.72; 435/7.8; 435/7.92; 435/15; 435/29; 435/68.1; 435/71.1; 435/128; 435/132; 435/174; 435/176; 435/177; 435/178; 435/179; 435/180; 435/181; 435/184; 435/188; 435/193; 435/194; 435/803; 435/814; 435/815; 435/961; 435/964; 436/501; 436/518; 436/524; 436/525; 436/526; 436/527; 436/528; 436/529; 436/530; 436/531; 436/532; 436/536; 436/541; 436/543; 436/544; 436/545; 436/564; 436/63; 436/103; 436/106; 436/161; 436/172; 436/815; 436/905; 424/601; 424/603; 514/151; 552/1; 552/3; 552/10; 552/12
(58) Field of Classification Search .................. 435/7.2, 435/7.4–7.8, 7.92, 15, 29, 128, 174, 803, 435/814, 964, 193, 132, 184, 188, 815, 68.1, 435/194, 71.1, 961, 176–181, 701, 96.1, 435/7.1; 514/151; 552/1–12; 436/501, 436/518, 543–546, 103, 106, 161, 536, 541, 436/63, 172, 815, 905; 424/601, 603
See application file for complete search history.

(56) References Cited

U.S. PATENT DOCUMENTS 5,783,709 A *  7/1998  Kress et al. ................ 548/535

(Continued)

FOREIGN PATENT DOCUMENTS

WO    WO 1996006609    3/1996

OTHER PUBLICATIONS

Lodish, et al. Molecular Cell Biology, 4th ed., W.H. Freeman & Co. (1999) (Section 3.5 attached herein).*

(Continued)

Primary Examiner—Long V. Le
Assistant Examiner—David J. Venci
(74) Attorney, Agent, or Firm—Fulbright & Jaworski L.L.P.

(57) ABSTRACT

The invention provides methods and compositions for azide tagging of biomolecules. In one embodiment of the invention, proteins are tagged by metabolic incorporation of prenylated azido-analog substrates. Examples of such analogs are azido farnesyl diphosphate and azido farnesyl alcohol. The azido moiety in the resulting modified proteins provides an affinity tag, which can be chemoselectively captured by an azide-specific conjugation reaction, such as the Staudinger reaction, using a phosphine capture reagent. When the capture agent is biotinylated, the resulting conjugates can be detected and affinity-purified by streptavidin-linked- HRP and streptavidin-conjugated agarose beads, respectively. The invention allows detection and isolation of proteins with high yield, high specificity, and low contamination without harsh treatment of proteins.

27 Claims, 5 Drawing Sheets

U.S. PATENT DOCUMENTS

| | | | | |
|---|---|---|---|---|
| 5,932,432 | A | 8/1999 | Crowell et al. | 435/15 |
| 5,952,473 | A | 9/1999 | Cohen et al. | 530/388.1 |
| 6,284,910 | B1 | 9/2001 | Spielmann et al. | 558/152 |
| 6,492,128 | B1 | 12/2002 | Haklai et al. | 435/7.2 |
| 6,570,040 | B1* | 5/2003 | Saxon et al. | 568/17 |
| 2002/0016003 | A1 | 2/2002 | Saxon et al. | 435/441 |
| 2004/0209317 | A1* | 10/2004 | Ting | 435/7.5 |
| 2005/0233389 | A1* | 10/2005 | Ting et al. | 435/7.5 |

OTHER PUBLICATIONS

Quellhorst, GJ. et al. Modification of Rab5 with a photoactivatable analog of geranylgeranyl diphosphate. J. Biol. Chem. 2001;276:40727-40733.*

Baron et al., "RhoB prenylation is driven by the three carboxyl-terminal amino acids of the protein: evidenced in vivo by an anti-farnesyl cysteine antibody," *Proc. Natl. Acad. Sci., USA*, 97:11626-11631, 2000.

Brems and Rilling, "Photoaffinity labeling of the catalytic site of prenyltransferase," *Biochemistry*, 18:860-864, 1979.

Chehade et al., "Photoaffinity analogues of farnesly pyrophosphate transferable by protein farnesyl transferase," J. Am. Chem. Soc., 124(8):8206-8219, 2002.

Chin et al., "An expanded eukaryotic genetic code," *Science*, 301:964-967, 2003.

End et al., "Characterization of the antitumor effects of the selective farnesyl protein transferase inhibitor R115777 in vivo and in vitro," *Cancer Res.*, 61:131-137, 2001.

Gibbs et al., "Novel farnesol and geranylgeraniol analogues: A potential new calss of anticancer agents directed against protein prenylation," *J. Med. Chem.*, 42:3800-3808, 1999.

Gololobov and Kasukhin, "Recent advances in the Staudinger reaction," *Tetrahedron*, 48:1353-1406, 1992.

Holmes, "Model studies for new o-nitrobenzyl photlabile linkers: substituent effects on the rates of photochemical cleavage," *J. Org. Chem.*, 62:2370-2380, 1997.

Kiick et al., "Incorporation of azides into recombinant proteins for chemoselective modification by the Staudinger ligation," *Proc. Natl. Acad. Sci., USA*, 99:19-24, 2002.

Lin et al., "Localization of isoprenylated antigen of hepatitis delta virus by anti-farnesyl antibodeis," *J. Gen. Virol.*, 80:91-96, 1999.

McGuire and Sebti, "Geranylgeraniol potentiates lovastatin inhibition of oncogenic H-Ras processing and signaling while preventing cytotoxicity," *Oconogene*, 14:305-312, 1997.

Melkonian et al., "Role of lipid modifications in targeting proteins to detergent-resistant membrane rafts. Many raft proteins are acylated, while few are prenylated," *J. Biol. Chem.*, 274(6):3910-3917, 1999.

Saxon et al., "Investigating cellular metabolism of synthetic azidosugars with the Staudinger ligation," *J. Am. Chem. Soc.*, 124:14893-14902, 2002.

Tamanoi et al., "Protein farnesylation in mammalian cells: effects of farnesyltransferase inhibitors on cancer cells," *Cell Mol. Life Sci.*, 58:1636-1649, 2001.

Tamanoi et al., "Farnesylated proteins and cell cycle progression," *J. Cel Biochem.*, 37:64-70, 2001.

Tsuda et al., "Stereospecific sythesis of a novel farnesyl protein transferase inhibitor, valinoctin A and its analogues," *J. Antibiot*, 49(10):1031-1035, 1996.

* cited by examiner

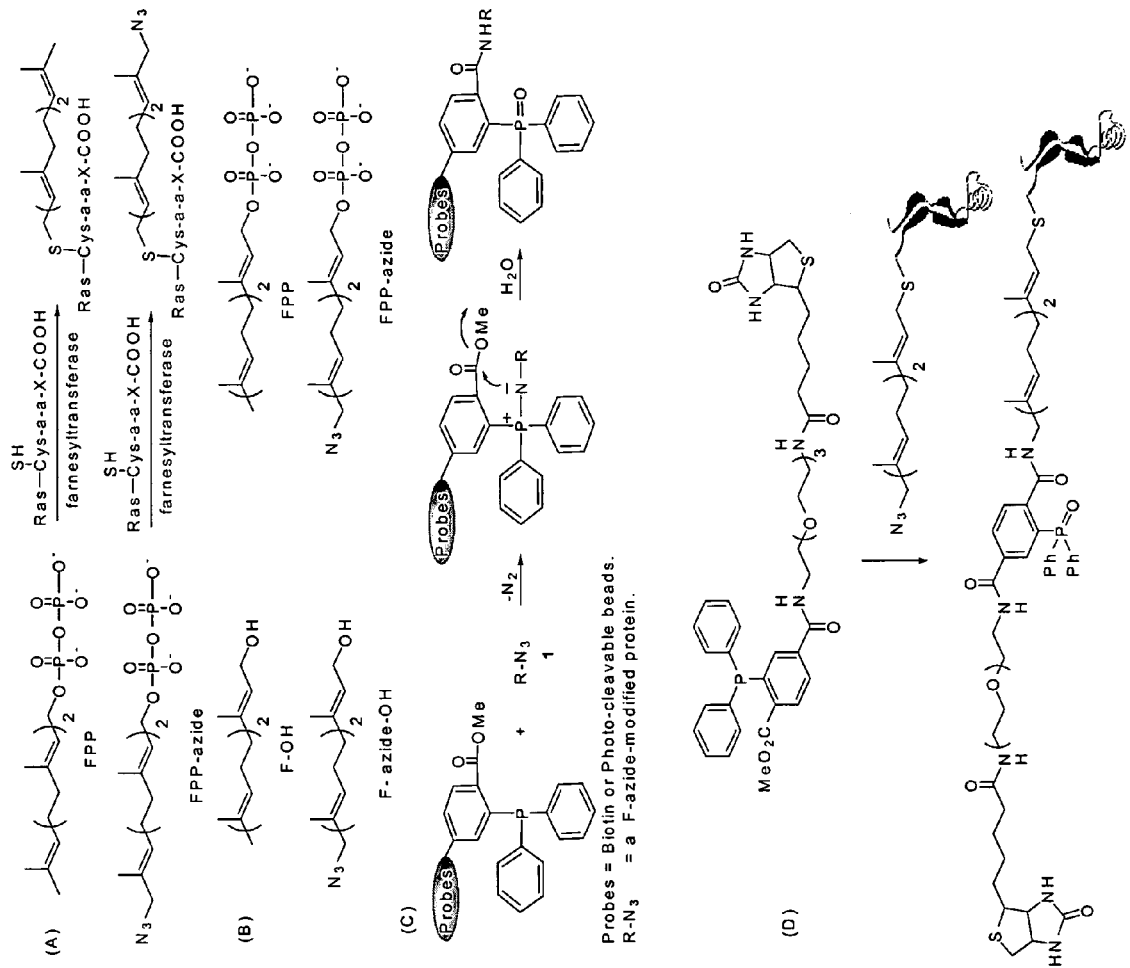
FIG. 1A-D

FIG. 3A-B
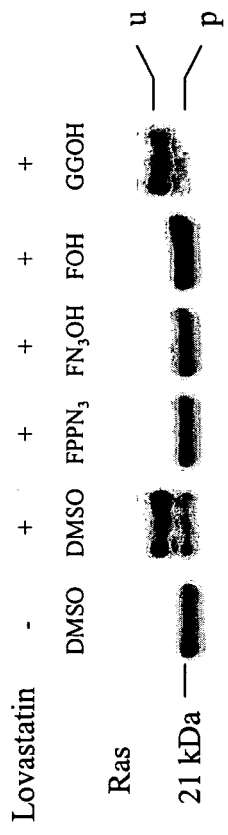
(A)
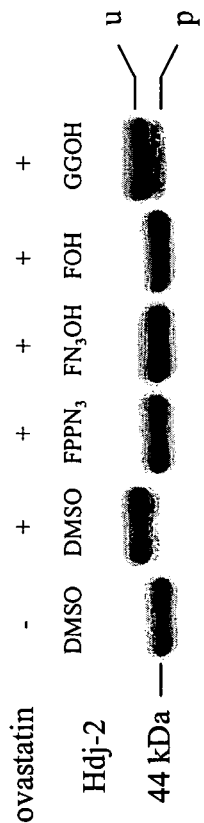
(B)

METHODS AND COMPOSITIONS FOR TAGGING VIA AZIDO SUBSTRATES

The government may own rights in the invention pursuant to grant number CA 85146 and GM 31278 from the NIH.

BACKGROUND OF THE INVENTION

1. Field of the Invention

The invention relates generally to the field of biochemistry. More specifically, the invention relates to tagging of biomolecules using synthetic azido substrates.

2. Description of Related Art

Protein isoprenylation is a general term of which protein farnesylation and protein geranylgeranylation are examples. It is a type of post-translational modifications involving the covalent attachment of polyisoprenoids, for example, a 15-carbon farnesyl or 20-carbon geranylgeranyl isoprenoid, typically through a thioether bond to a C-terminal cysteine residue of proteins (Fu, 1999). To date, three enzymes are known to isoprenylate proteins, viz., protein farnesyltransferase (FTase) (Reiss, 1990), protein geranylgeranyltransferase type I (GGTase-I) (Seabra, 1991) and protein geranylgeranyltransferase type II (GGTase-II) (Moores, 1991). FTase utilizes farnesyl diphosphate (FPP) and selectively alkylates the cysteine residue fourth from the C-terminus in a conserved isoprenylation motif designated the "CAAX box", where "C" is a cysteine residue, "A" as an aliphatic residue, and "X" is either S, M, Q, A, or T (single-letter amino acid codes). GGTase-I and GGTase-II are responsible for linking a geranylgeranyl group, from geranylgeranyl diphosphate (GGPP), to a cysteine residue in the C terminal CAAX (where X is L or F), CC, or CXC motifs of the proteins (Fu, 1999). Isoprenylation promotes membrane association of the target proteins and protein-protein interactions, and is essential for the function of the modified proteins (Fu, 1999; Tamanoi, 2001).

A variety of proteins are farnesylated, including the Ras superfamily G-proteins. The post-translational modification is required for the activation of Ras proteins and their transforming potential (Fu, 1999). For this reason, farnesyltransferase has been hypothesized as an anti-tumor drug target. Farnesyltransferase inhibitors (FTIs) that inhibit FTase have been developed as potential cancer therapeutic agents and a few FTI compounds are currently under clinical evaluation (End, 2001; Tamanoi, 2001).

Efficient methods for the detection and quantification of protein prenylation are needed for the analysis of the dynamics of protein prenylation. Metabolic incorporation of radioisotope labeled farnesyl pyrophosphate (FPP) has been used to detect farnesylated proteins, but is expensive and inconvenient (Melkonian, 1999; Gibbs, 1999). Anti-farnesylation antibodies have also been developed, but they have not been widely used, largely due to limited binding affinity and specificity (Lin, 1999; Baron, 2000). Neither approach is able to adequately enrich the farnesylated proteins from a complex protein mixture.

Global profiling of farnesylated proteins under diverse cellular environments with FTI treatments would reveal those farnesylated proteins with a change in farnesylation modification, and would reveal likely protein targets for several FTIs currently under clinical trials. This would allow characterization of the dynamics of farnesylated proteins in response to changes of cellular environment. Proteomics analysis is usually performed by 2D-gel/mass spectrometry- (Hanash, 2003) or ICAT/mass spectrometry-based proteomic methods (Gygi, 1999; Aebersold, 2003), which is typically limited to a few thousand of the most abundant proteins (Aebersold, 2003). Due to their low-to-medium abundant expression, farnesylated proteins are usually not detected, and, therefore, not quantified by these methods when whole-cell protein lysates are used as starting materials. Thus, efficient proteomic analyses of these proteins require an enrichment technology that is able to remove non-farnesylated proteins and reduces the complexity of the protein mixture. Unfortunately, such a method has not previously existed. There is, therefore, a great need in the art for techniques that may be used for purification or enrichment of farnesylated and similarly modified proteins.

SUMMARY OF THE INVENTION

In one aspect, the invention provides a method for detecting at least a first isoprenylated protein in a cell comprising: a) obtaining a synthetic isoprenyl azide substrate of at least a first protein in said cell; b) contacting the cell under conditions wherein the cell takes up and incorporates into the protein at least a first azide from the substrate; and c) detecting at least said first protein from proteins produced by said cell with a phosphine capture reagent by the Staudinger reaction. In the method, the protein may be farnesylated. Detecting may comprise isolating the first protein. In one embodiment of the method, FPP is inhibited in the cell. FPP may be inhibited, for example, by contacting the cell with an HMG Co-A reductase inhibitor, including lovastatin. In certain embodiments of the invention, the prenyl azide is an azido farnesyl diphosphate, and/or azido farnesyl alcohol. The protein may be native to said cell.

In certain embodiments of the invention, the step of detecting comprises Western blot analysis. The phosphine capture reagent may be bound to a solid support, including by a photocleavable linker. The phosphine capture reagent may comprise a label, including a fluorescent, colorimetric, chemiluminescent, or radioactive label and further including antigens. An antigen may be biotin and the method may comprise affinity-purification with streptavidin- and/or avidin-conjugated beads. The beads, for example, may comprise silica gel, polystyrene, starch, sugars, or organic or inorganic matrixes. In further embodiments of the invention, a nucleophile in the Staudinger reaction is immobilized on a polymer, for example, mono-methyl polyethylene oxide, SEPHAROSE, TENTAGEL, AGROGEL-Wang, polysaccharide, polystyrene, polyethane, and co-polymers thereof. The method may comprise detecting a plurality of proteins. Ras is one example of a protein that may be detected.

In further embodiments of the invention, a substrate includes one of the following formulas presented below. The invention also provides compositions comprising at least one of these molecules.

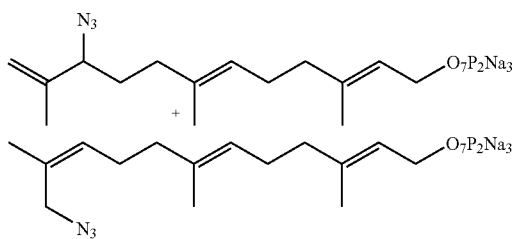

-continued

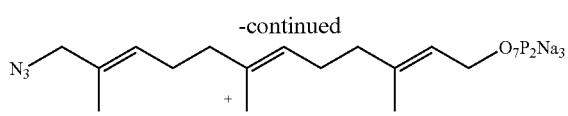

In yet another aspect, the invention provides a method for labeling a protein in a cell, comprising: a) preparing a synthetic substrate of said protein comprising at least a first azide; and b) contacting the cell under conditions wherein the synthetic substrate is taken up and incorporated into the protein and wherein the protein is labeled with said first azide. In the method, the synthetic substrate may be prenylated.

The following abbreviations have been used herein: BPPCR, biotinylated phosphine capture reagent; DMSO, Dimethyl sulfoxide; FTase, farnesyltransferase; FOH, farnesyl alcohol; F-azide, azido-farnesyl; F-azide-OH (FN₃H), azido-farnesyl alcohol; FPP, farnesyl diphosphate; FPP azide (FPPN₃), azido farnesyl diphosphate; FTIs, farnesyltransferase inhibitors; GG-OH, geranylgeranyl alcohol; GGPP, geranylgeranyl diphosphate; HPLC, high-performance liquid chromatography; MS/MS, tandem mass spectrometry; and TAS, Tagging-via-Azido-Substrate.

BRIEF DESCRIPTION OF THE DRAWINGS

These and other features, aspects, and advantages of the present invention will become better understood with regard to the following description, appended claims, and accompanying figures.

FIG. 3. Detection of F-azide modified Ras and HDJ-2 by mobility-shift assay. Mobility-shift assay of Ras (A) and HDJ-2 (B). COS-1 cells were labeled with the indicated compounds for 24 h, the cell lysate were resolved in SDS-PAGE and probed using anti-Ras and anti-HDJ-2 antibodies, respectively. The letters, "u" and "p", indicate the unmodified and isoprenylated forms of the protein, respectively.

DETAILED DESCRIPTION OF THE INVENTION

Figure 1E:
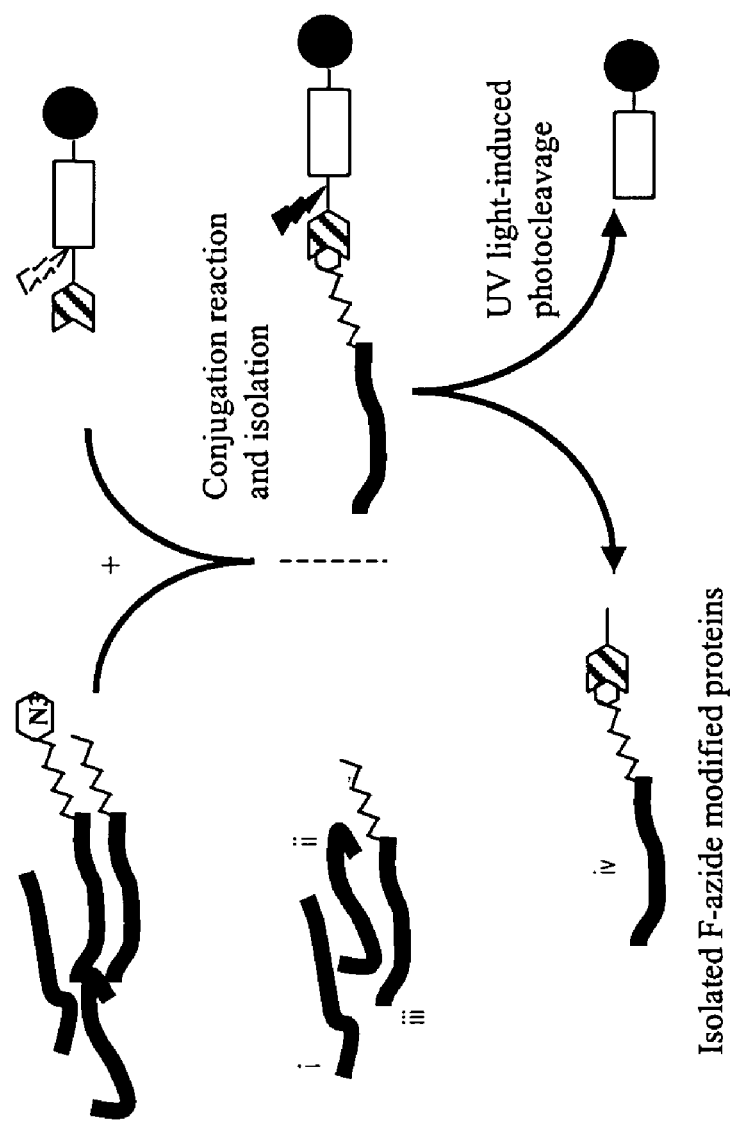
FIG. 1. Schematic representation of one embodiment of the TAS technology for solid-phase-isolation of azide-labeled farnesylated proteins. (A) Farnesyltransferase-catalyzed enzymatic reaction using FPP or FPP azide as a substrate. (B) Chemical structures of natural FPP, and a FPP-azide and the corresponding alcohols, F-OH (farnesol) and F-azide-OH. (C) A Staudinger conjugation reaction between a phosphine and an azide-containing molecule. (D) The structure of a biotinylated phosphine capture reagent and its reaction product with an azido-farnesylated protein. (E) Experimental procedure for the isolation of F-azide modified proteins. Protein i and ii, unmodified proteins; protein iii, a protein modified by natural farnesyl group; and protein iv, F-azide modified proteins. Only F-azide modified protein iv is purified and released by UV light-induced photocleavage.

The invention provides Tagging-via-Azido-Substrate (TAS) technology for the tagging and isolation of selected proteins. The invention, in particular embodiments, allows detection and isolation of farnesylated proteins by metabolic incorporation of a synthetic azido-farnesyl analog, such as azido farnesyl diphosphate (FPP-azide) or azido farnesyl alcohol (F-azide-OH), as a replacement of the natural substrate, FPP, in a cellular pathway for protein farnesylation. The azido moiety in the resulting farnesyl-azide (F-azide)-modified proteins provides a tag, which can be chemoselectively captured by an azide-specific conjugation reaction, for example, the Staudinger reaction and subsequent intramolecular interception of the iminophosphorane intermediate by an ester or other suitable functionality. The resulting conjugates can be detected and/or purified, for example, using streptavidin-linked- HRP or agarose beads. Since the purification relies on covalent bond formation during a specific, efficient conjugation reaction between an azide and a phosphine capture reagent, other proteins without F-azide modification can be effectively removed by thorough washing, centrifugation or other means.

TAS technology allows farnesylated proteins to be detected with high yield and high specificity. For example, it was demonstrated that (1) FPP-azide or F-azide-OH was used by cells for protein farnesylation; and (2) The F-azide modified proteins could be specifically detected by Western blotting analysis. The techniques of the invention will find wide applications for detection, quantification, and proteomics analysis of farnesylated proteins. The methods and compositions described can be extended to other post-translational modifications, including geranylgeranylation and glycosylation, expanding the scope for detection, quantification, and proteomics analysis of post-translationally modified proteins.

The inventors describe the design and synthesis of azido-farnesyl substrates for protein farnesylation and ability of the compounds to enter into the cells and then incorporate into the proteins that contain farnesylation consensus sequence. The farnesyl transferase was shown to be tolerant of an azido tag on the farnesyl. Metabolic incorporation of azido-farnesyl groups into farnesylated proteins could be increased by inhibition of endogenous synthesis of FPP by blocking HMG Co-A reductase using lovastatin. The metabolic labeled, azido-prenyl-modified proteins could be conjugated to phosphine capture reagents linked to detection or affinity-purification reagents, such as biotin, or other molecules allowing ready detection and isolation of the conjugate. While FPP analogues are charged and hydrophilic, and appear to be difficult to penetrate cell plasma membrane, they were shown to be used by the cell and reverse lovastatin inhibition (Gibbs, 1999). In addition, F-OH analogs have been used to dose the cells, and the cellular machine was able to convert the compounds into FPP analogs for protein farnesylation (McGuire, 1997; Gibbs, 1999). It is believed that both FPP azide and F-azide-OH described in this work were used by the cells likewise.

Several lines of evidence indicate that F-azide modified proteins maintain the major characteristics of naturally farnesylated proteins. First, F-azide-modified Ras retains GTPase activity. Second, F-azide modification induced Ras' membrane association. Finally, the cells cultured in DMEM media containing lovastatin, FPP-azide/F-azide-OH, and GG-OH, have comparable growth rate with those cultured without these compounds.

The TAS technology provides a number of advantages. First, the TAS technology allows uniformly chemoselective enrichment of proteins containing azide moiety utilizing phosphine capture reagents. Chemoselective conjugation is based on a reaction between the phosphine capture reagent and the azide, and does not depend on the surrounding structural elements in the protein. Any protein with the F-azide modification will participate as long as the azide group is accessible for chemoselective conjugation reaction. In contrast, the binding affinities of antibodies to farnesylated proteins are peptide sequence-dependent and can only recognize a subset of farnesylated proteins. Second, the Staudinger reaction is performed under such mild conditions that proteins and their modifications will not be changed. Third, the conjugation reaction is very specific between azide and phosphine capture reagents. Moreover, the TAS technology allows purification of proteins containing azide moiety with low contamination. Due to covalent bonding nature resulting from the reaction between the azide and the phosphine capture reagent, both non-specifically binding proteins and F-azide-modified proteins' binding proteins can be extensively resolved or separated using stringent washing buffers, such as (1) high-detergent buffer, (2) denaturing zwitterionic buffer (e.g. 8.0 M urea), or (3) high-salt buffer. Finally, the TAS technology in combination with existing proteomics methods (e.g., 2D-gel/mass spectrometry (Hanash, 2003), multiple-dimensional MS (Wu, 2003), and/or ICAT/MS (Aebersold, 2003; Gygi, 1999) allow efficient analysis of dynamic farnesylation modification.

A modification of the described phosphine capture reagent may be used to make the TAS technology more convenient in some cases for the isolation of farnesylated proteins. The phosphine capture reagent can be linked to solid beads with photocleavable linkers, allowing isolation of the proteins under very mild conditions. Given the fact that only about 100 proteins are farnesylated and most of them are present in low-to-medium abundance, the technology can easily achieve more than 200-fold purification of the modified proteins if it is assumed that 20,000 proteins are expressed in a cell. This improvement makes existing proteomics method a very practical approach for the identification and quantification of low-abundant, farnesylated proteins in the range of a few hundred copies per cells. The temporal application of the TAS technology, when coordinated with drug treatments or signal challenges, allows correlation of the physiological response with the farnesylation of specific pools of proteins and will allow for isolation and identification of the individual protein targets. The described technology is well-suited for the characterization of biological functions and identification of farnesylated-proteins targets in response to drugs under clinical application or clinical evaluation, such as farnesyl transferase inhibitors and statins.

Analysis of dynamic posttranslational modifications is notoriously challenging due to difficulty in detecting modified peptides and the unavailability of a highly selective method for enriching modified proteins. Due to the small size of the azide moiety, it is likely most of the azido-modified versions of substrates for protein modification will be metabolically incorporated into proteins. The inventors have demonstrated that a similar strategy worked for glycosylation. It is thus indicated that the TAS technology will find a wide application toward the efficient proteomics analysis of post-translationally modified proteins by reducing dynamic range and the complexity of the proteome.

In one embodiment of the invention, azide tagging involves: (1) metabolic labeling of farnesylated proteins by feeding of cells with azido-containing synthetic substrates, for example, FPP azide or F-azide-OH, while inhibiting the endogenous synthesis of FPP, the natural substrate for protein farnesylation; (2) chemoselective capture of the F-azide-modified proteins using a phosphine capture reagent involving a Staudinger reaction; and (3) detection or isolation of the conjugated products.

Synthetic substrates, such as FPP azide or F-azide-OH, are designed in such way that they are similar enough to natural substrates so that endogenous enzymatic pathways will use them efficiently for protein modification. Importantly, the substrates contain an azide tag for chemoselective conjugation and selective purification. Organic azides are well-suited for tagging biological molecules for several unique features. The azide functional group is comparatively small, uncharged, non-polar, air-stable, and abiotic. The azide moiety has not been found in enzymatically produced molecules, including small organic molecules and biomolecules (proteins or nucleotides) in living organisms. Moreover, azides are only slowly reduced to amines by thiols (Staros, 1978) under physiologic conditions and are otherwise relatively inert in biologic milieu. The toxicity associated with organic azides is likely tolerated within the ranges of experimental time window as azide-containing molecules have been used in therapeutics (e.g., AZT) and various biological studies (Saxon, 2002; Chin, 2003).

The reduction of organic azides to amines using phosphorus(III) compounds was first described in 1919 and is now known as the Staudinger reaction (Gololobov, 1992). Typically, aryl-substituted phosphorus reagents, e.g., triphenylphosphine, are used because of their chemical stability as alkylphosphines are pyrophoric and decompose violently in contact with water. Reaction of azide 1 with P(III)-reagent 2, usually at room temperature, proceeds with the loss of nitrogen and initially generates adduct 3 that can be depicted as an iminophosphorane or an aza-ylide. Subsequent hydrolysis of 3 affords amine 4 and phosphine oxide 5.

In certain embodiments of the invention, solid supports may be used in conjunction with an azide capture agent. A solid support used in accordance with the invention can comprise potentially any suitable material. Examples of such materials include, but are not limited to, polymers, plastics, resins, polysaccharides, silica or silica-based materials, carbon, metals, inorganic glasses, membranes, etc. In certain embodiments of the invention, the solid support may be formed into beads.

A detection or other agent may be bound to the solid support using a linker. Many linkers are known in the art, including UV-cleavable linkers, amide linkages, ester link ages, thioester linkages, ether linkages, thioether linkages, phosphoester linkages, phosphoramide linkages, anhydride linkages, disulfide linkages, ionic and hydrophobic interactions, bispecific antibodies and antibody fragments, or combinations thereof.

In certain embodiment, protein isolation techniques may be used to isolate azido-tagged proteins. Techniques for protein isolation are well known to those of skill in the art and include ammonium sulfate precipitation, immuno precipitation, ethanol or acetone precipitation, acid extraction, ion exchange chromatography, size exclusion chromatography, affinity chromatography, high performance liquid chromatography, electrophoresis, thin layer chromatography, and ultra filtration. If required, protein refolding systems can be used to complete the configuration of the protein.

The detailed description set-forth above is provided to aid those skilled in the art in practicing the present invention. Even so, this detailed description should not be construed to limit the present invention as modifications and variation in the embodiments discussed herein can be made by those of ordinary skill in the art without departing from the spirit or scope of the present inventive discovery.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Azide-containing Proteins can be Chemoselectively Conjugated by Arylphosphine Capture Reagents by the Staudinger Reaction The reduction of organic azides to amines using phosphorus(III) compounds was first described in 1919 and is now widely known as the Staudinger reaction (Gololobov, 1992). Typically, aryl-substituted phosphorus reagents, e.g., triphenylphosphine, are used because of their chemical stability, as alkylphosphines are pyrophoric and decompose violently in contact with water. Reaction of azide 1 with P(III)-reagent 2, usually at room temperature, proceeds with loss of nitrogen and initially generates adduct 3 that can be depicted as an iminophosphorane or an aza-ylide. Subsequent hydrolysis of 3 affords amine 4 and phosphine oxide 5.

Arylphosphines are comparatively inert towards most enzymatic processes (Kiick. 2002). Their utility as "selectively addressable" in vivo labeling agents has been demonstrated in a series of experiments in which biochemical probes were attached or ligated to azide-modified proteins and cell-surface sialosides (Saxon, 2002; Kiick, 2002). The key step in each case exploited a Staudinger reaction (equation 2—see eq 2 below), The intermediate aza-ylide 7, arising from addition of azido-conjugate 1 to a substituted arylphosphine 6, was intercepted by the adjacent methyl ester and ultimately furnished the stable wide 8.

Probes = Biotin or Photo-cleavable beads.
R—N$_3$ = a F-azide-modified protein.

Example 2

FPP-azide is a Substrate for Protein Farnesylation In Vitro

To determine whether farnsyltransferase can use FPP azide as a substrate for protein farnesylation, an in-vitro enzymatic reaction was carried out between a CAAX-box containing peptide (RC peptide, KKFFCAIS) and FPP azide. The peptide was shown to be farnesylated in vitro (Yokoyama, 1991).

Figure 2:
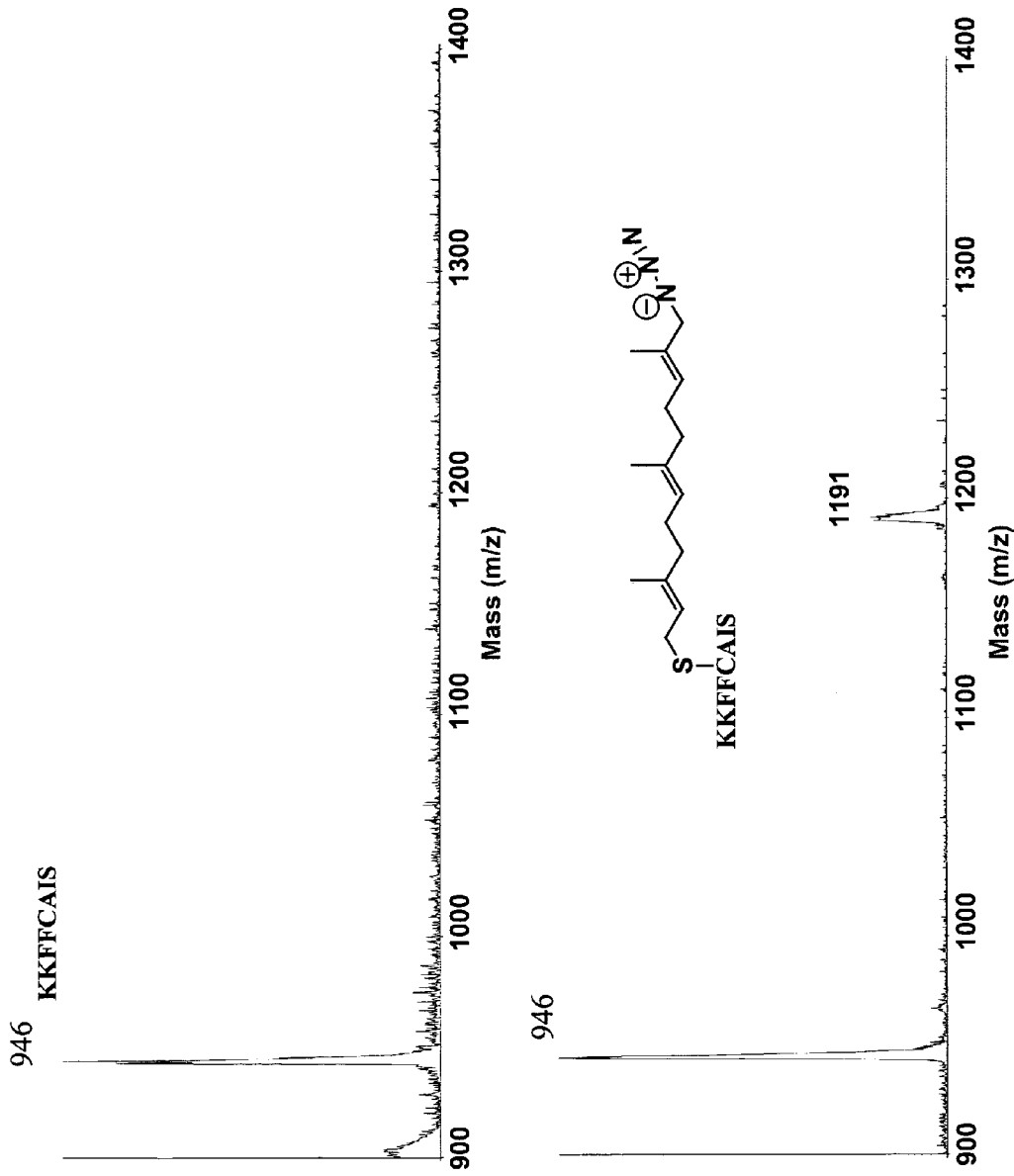
FIG. 2. FPP azide is a substrate for in vitro farnesylation reaction. MALDI-TOF mass spectra of RC peptide before (A) and after (B) in vitro farnesylation reaction. One hundred pmol RC-peptide (KKFFCAIS) were mixed with 3000 pmol FPP azide and 35 pmol FTase in 7 µl reaction buffer and incubated at 30° C. for 10 h. The F-azide modified RC-peptide was confirmed by mass spectrometry (m/z, 1191).

The molecular masses of the peptide prior to and after enzymatic reaction were determined by MALDI-TOF mass spectrometry. F-azide-modified peptide was detected after enzymatic reaction (m/z, 1191 Da, a mass increase of 246 Da over RC peptide) (FIG. 2).

In a parallel study, an enzymatic reaction was carried out with FPP, the natural substrate for protein farnesylation. It was found that the reaction rate between the RC peptide and FPP azide 16 was somewhat faster than that between the RC peptide and FPP. These studies indicate that FPP azide 16 is a good substrate for the farnesyltransfer reaction in vitro.

Example 3

Ras and HDJ-2 can be Farnesylated by Exogenous Azido-farnesyl Substrates in vivo To determine if the cell will process exogenous azido-farnesyl substrates, metabolic labeling of cells was carried out with synthetic substrates, either FPP azide or F-azide-OH, and mobility-shift assays were performed for Ras and HDJ-2 in order to determine if they are posttranslationally modified. Unprocessed Ras and HDJ-2 move more slowly than their farnesylated isoforms, therefore allowing separation in SDS-PAGE and subsequent detection by Western blotting analysis (James, 1994; Adjei, 2000).

Lovastatin, a HMG CoA reductase inhibitor, blocks mevalonate synthesis, and therefore leads to inhibition of FPP synthesis and protein farnesylation (Sinensky, 1990; Kim, 1990). As expected, lovastatin was found to induce mobility shift of both Ras and HDJ-2 to higher MW regions, suggesting inhibition of endogenous farnesylation. Metabolic labeling of the cells with either FPP azide or F-azide-OH, however, reversed the mobility shift, suggesting protein farnesylation were restored. As a control, GG-OH was found to not affect the mobility shifts of the proteins (FIG. 3).

Farnesylated Ras protein is plasma-membrane associated while the unprocessed isoform is mainly located in cytosol. As expected, Ras was mainly detected in cytosol when the cells were treated with lovastatin. On the other hand, either FPP-azide or F-azide-OH were able to restore membrane association. The results indicate that both FPP azide and F-azide-OH can be used by cellular metabolic pathway for protein farnesylation.

Example 4

Figure 4:
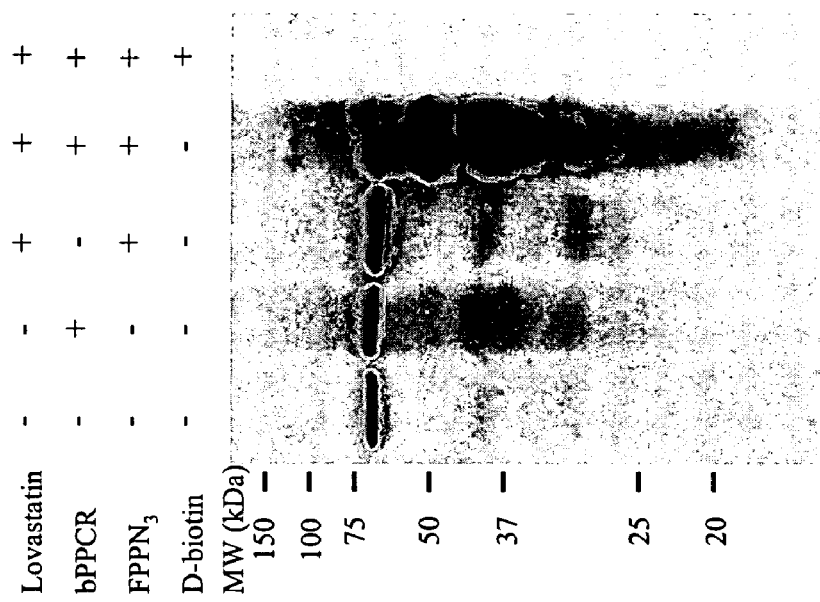
FIG. 4. Global detection of F-azide modified proteins by Western blotting analysis. COS cells were labeled with DMSO, or FPP N3 with or without lovastatin, as indicated, for 24 h. The protein lysates from the cells were precipitated by acetone/TCA method, redissolved in a buffer containing 2% SDS and PBS. The resulting solution was conjugated to biotinylated phosphine capture reagents or not, precipitated by acetone/TCA method again. The protein pellet was redissolved in 1×SDS sample buffer, resolved in SDS-PAGE, and detected by Western blotting analysis using streptavidin-conjugated HRP with or without biotin.

Metabolic Incorporation of FPP-azide and F-azide-OH into Proteins in Cultured COS Cells To further test whether proteins could be modified by F-azide and subsequently detected, Western blotting analysis was carried out in order to detect F-azide modified proteins. The protein whole-cell lysate from the cells dosed with lovastatin and FPP azide was subjected to conjugation reaction using biotinylated phosphine capture reagent. The resulting lysate was resolved using a SDS-PAGE gel and the biotinylated proteins detected by Western blotting analysis using HRP-conjugated streptavidin. Dosing the cells with either FPP azide or F-azide-OH resulted in the detection of multiple proteins, which could be competed away by 0.1 mM D-biotin, suggesting the signals detected were azide-specific. The results indicate that multiple proteins beyond Ras and HDJ-2 can be farnesylated by F-azide and detected by Western blotting analysis. Since FPP-azide and F-azide-OH have similar labeling efficiency, only FPP-azide was used in the subsequent studies (FIG. 4).

Example 5

Metabolic Incorporation of F-azide into the Known Farnesylated Proteins

To further demonstrate F-azide modification in proteins, two known, farnesylated proteins (HDJ-2 and Ras) were immunoprecipitated with their corresponding antibodies. The resulting immunocomplexes were resolubilized in 1×SDS sample buffer and then subjected to conjugation reaction using biotinylated phosphine capture reagents, respectively. The free biotinylated capture reagent was removed by a desalting column, resolved in SDS-PAGE, and then detected by Western blotting analysis HRP-conjugated HRP. Protein signals corresponding molecular weights of HDJ-2 and Ras were detected from the cells dosed with FPP-azide but not in the control cells. These results indicate that HDJ-2 and Ras could be metabolically labeled by F-azide.

Example 6

Isolation and Proteomics Analysis of F-azide-modified Proteins

Isolation of F-azide-modified proteins is achieved based on the reaction between biotinylated phosphine capture reagent and the azide moiety in the F-azide modified proteins. Therefore, only F-azide-modified proteins are isolated while proteins modified by the natural farnesyl group (background level) and the unmodified isoforms are not be isolated.

Due to high binding affinity between biotin and streptavidin, other non-conjugated proteins could be removed by exhaustive washing with high-detergent and 8.0 M urea buffers. The affinity-purified proteins are then subjected to in-solution trypsin digestion and the resulting tryptic peptides subjected to nano-HPLC/MS/MS analysis for proteins identification. In parallel, conjugation reactions are also performed and affinity-purification carried out for control cells without FPP-azide labeling. The control experiment is able to identify endogenous biotinylated proteins, which are subtracted from the proteins identified from the cells labeled with FPP azide. Analysis of F-azide-modified proteins is carried out from dishes of cells leading to the identification of F-azide-modified proteins.

Isolation and mass spectrometric identification of farnesylated proteins. The phosphine capture reagent will be conjugated to F-azide-modified proteins from cells incubated with FPP azide. The conjugated F-azide modified proteins will be isolated and subsequently released by a photo-cleavage reaction. A typical procedure involves growing dishes (10 cm) of COS-1 cells to 70% confluency. Protein whole cell lysate will be prepared as described below. Since labeling efficiency between F-azide-OH and FPP-azide is similar, FPP-azide was selected for use in the subsequent studies.

Twenty dishes (15 cm) of COS-1 cells are grown in Dulbecco's modified Eagle's medium supplemented with 10% fetal bovine serum, and 1% penicillin/streptomycin in a humidified atmosphere with 5% $CO_2$ at 37° C. until ~70% confluence. Twenty five μM lovastatin, 10 μM FPP azide, and 10 μM GGOH will be added to the cell culture medium, and the cells will be labeled for 15 h.

GGOH is a natural substrate for protein geranylgeranylation. It was shown that GGOH can be converted into GGPP, the natural substrate for GGTase, for protein geranylgeranylation in the cell. The compound was shown to prevent cytotoxicity of FTI.

The resulting cells are harvested and lysed in 5 mL of lysis buffer (50 mM HEPES pH 7.6, 150 mM sodium chloride, 1.5 mM magnesium chloride, 1 mM EDTA, 1 mM DTT, 1%

SDS, and protease inhibitor cocktail (Roche Molecular Biochemicals, Indianapolis, Ind.)). The suspension is clarified by centrifugation at 15,000×g for 5 min.

For isolation of F-azide modified proteins, the protein extract is precipitated by the acetone/TCA precipitation method to remove unused FPP azide. The protein pellet is then redissolved in the lysis buffer and mixed with a suitable amount of phosphine capture reagent linked to photo-cleavable beads. The resulting suspension is then incubated with agitation at rt for 10 h. After conjugation, the resulting suspension is centrifuged at 3000×g for 5 min and the supernatant removed. The beads are washed extensively with washing buffer I (Tris-Cl, pH 7.5, KCl 100 mM, SDS 1%, 1×protease inhibitor cocktail) twice, washing buffer II (Tris.Cl, pH 7.5, 8.0 M Urea, 1×protease inhibitor cocktail) twice, and then twice with PBS buffer.

The proteins captured on the beads are released by irradiating the beads with 360 nm light from a Blak-Ray long-wave UV lamp (100 W, available from VWR Scientific, West Chester, Pa.). 360 nm light will induce cleavage of the photolabile linker present in the capture reagent (Rinnova, 2000). The irradiation time is optimized based on the amount of recoverable protein obtained from the beads. The supernatant containing the photo-cleaved proteins is collected and precipitated using acetone/TCA.

High-concentration SDS and urea can be used in order to disrupt protein-protein interactions and efficiently remove non-specific proteins. Almost all the protein-protein interactions will be disrupted by the harsh washing conditions. Since the F-azide modified proteins are covalently conjugated to the beads, the proteins will not be removed by the harsh washing conditions.

The protein pellet obtained above is resuspended in a digestion buffer (50 mM $NaHCO_3$ (pH 8.0), 0.5% CHAPs, 10 mM DTT). The protein concentration is determined by a DC Protein Assay kit (BioRad Laboratories, Hercules, Calif.), which is detergent compatible. The protein solution is digested with 2% of sequence-grade trypsin (w/w) at 37° C. overnight. The tryptic peptides will be cleaned using C18 zipTip column and dried in a SpeedVac. The dried sample will be resuspended in HPLC A buffer and analyzed by HPLC/MS/MS for protein identification.

The isolation and identification of geranylgeranylated proteins is performed in the same way as described for farnesylated proteins except that the cells are dosed with either GG-azide-OH or GGPP azide, in combination with lovastatin, and FPP. FPP is added to reduce the potential toxicity of lovastatin. In this embodiment, only geranylgeranylated proteins will be modified by the azide moiety (in GG-azide group) due to GG-azide-OH or GGPP azide used.

Example 7

Materials and Methods

A. Materials

The reagents used included: lovastatin from Sigma-Aldrich (St. Louis, Mo.); penicillin/streptomycin, fetal bovine serum and Dulbecco's modified Eagle's medium (DMEM), fetal bovine serum, trypsin, and penicillin/ streptomycin from Life Technologies (Gaithersburg, Md.); the protease inhibitor cocktail from Roche Molecular Biochemicals (Indianapolis, Ind.); lovastatin, trans-farnesol, and all trans-geranylgeraniol from Sigma-Aldrich (St. Louis, Mo.); bovine serum albumin; dithiothreitol (DTT) from Fisher Scientific Corp. (Pittsburgh, Pa.); immobilon transfer membranes (PVDF) from Millipore (Bredford, Mass.); Western Lightning Chemiluminescence Reagent Plus from Perkin Elmer Life Science (Boston, Mass.); Bio-Rad DC protein assay kit from Bio-Rad Laboratories (Hercules, Calif.); anti-Ras from BD Transduction laboratories (San Diego, Calif.); anti-HDJ-2 antibody from NeoMarkers (Fremont, Calif.); anti-Lamin B, anti-Rheb antibody, and anti-goat IgG from Santa Cruz Biotechnology (Santa Cruze, Calif.); streptavidin-HRP from Amersham Pharmacia Biotech (Piscataway, N.Y.); immunoPure D-biotin from Pierce Biotechnology (Rockford, Ill.); and horseradish peroxidase-conjugated anti-mouse IgG from Sigma-Aldrich (St. Louis, Mo.).

B. Synthesis of F-azide-OH and FPP Azide

F-azide-OH 12a, 12b and 12C, along with FPP azides 15a, 15b and 15c were efficiently prepared as summarized in Scheme 1. Commercial trans, trans-farnesyl acetate 9 was converted to a mixture of allyl alcohols 10a and 10b by treatment with t-BuOOH and $SeO_2$ along with some other minor products (Zoretic, 1996). The by-products were then removed chromatographically and the mixture of allyl alcohols 10a and 11b was converted into azides 11a, 11b and 11c in good combined yield using $Ph_3P$, diisopropyl azodicarboxylate (DIAD) and $(PhO)_2P(O)N_3$. Hydrolysis of the acetate of 11a, 11b and 11c in MeOH afforded F-azide-OH 12a, 12b and 12c in excellent yield. Exposure of 12a, 12b and 12c to N-chlorosuccinimide (NCS) in dimethyl sulphoxide furnished chloro-farnesyl azides 13a, 13b and 13c, respectively, in good yield. The inseparable mixture of 13a, 13b and 13c was smoothly converted to pyrophosphates 14a, 14b and 14c in excellent yield by displacement with $(Bu4N)_3HP_2O_7$ in acetonitrile according to the published procedure (Davisson, 1985). The n-tetrabutylammonium pyrophosphate azides 14a, 14b and 14c were further transformed to ammonium pyrophosphate azides 15a, 15b and 15c in good yield by passing through an ammonium Dowex 50X8-400 ion exchange column. Finally, 15a, 15b and 15c were converted in excellent yield to the final products, sodium salts of pyrophosphate azides 16a, 16b and 16c, by passing through a $Na^+$ Dowex 50×8-400 ion exchange column.

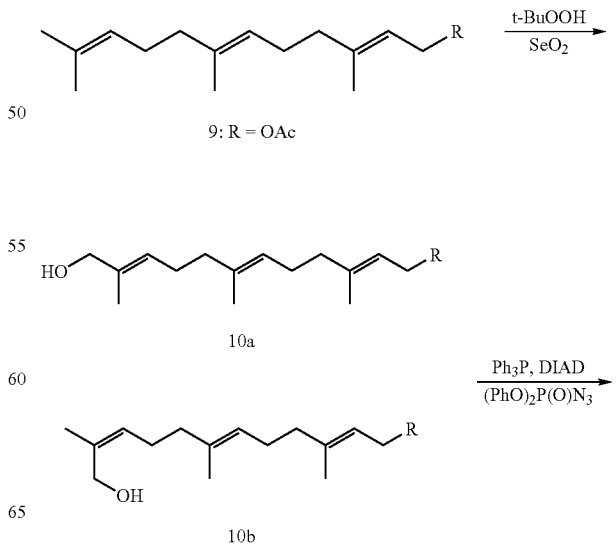

Scheme 1

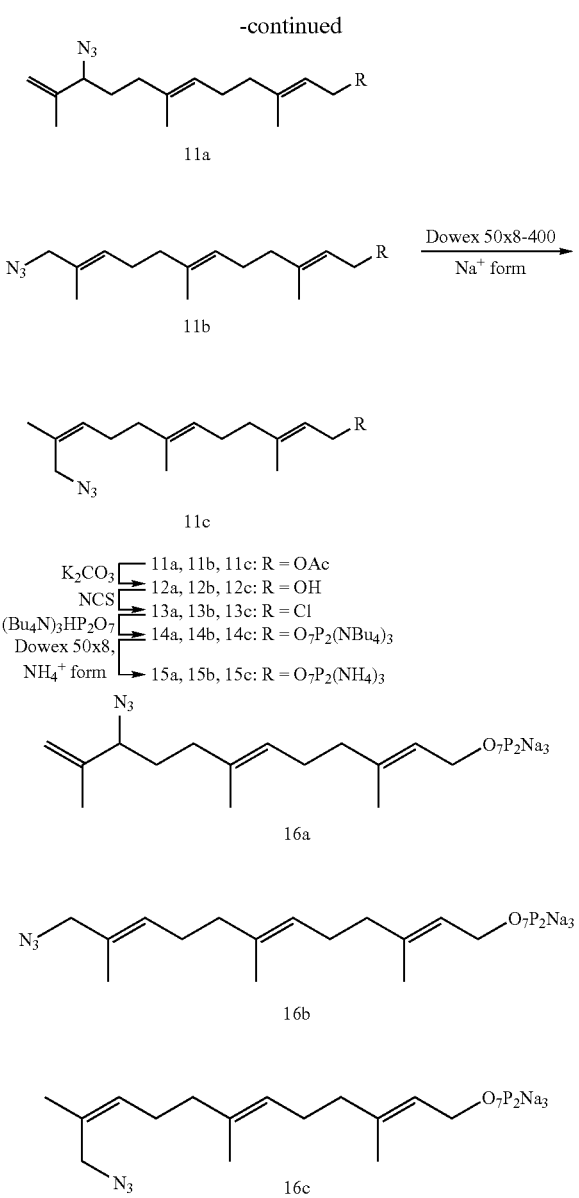

C. In-vivo Labeling of Proteins with FPP Azide

COS-1 cells were grown in Dulbecco's modified Eagle's medium supplemented with 10% fetal bovine serum, 1% penicillin/streptomycin. When cells reached to 70% confluence, lovastatin was added and incubated for suitable amount of time prior to adding FPP azide.

D. Western Clotting Analysis of Farnesylated Proteins

Cells were harvested and lysed in 1 ml of lysis buffer (50 mM HEPES pH 7.6, 250 mM sodium chloride, 1.5 mM magnesium chloride, 1 mM EDTA, 10% (v/v) glycerol, 1% Triton X-100, and protease inhibitor cocktail (Roche Molecular Biochemicals, Indianapolis, Ind.)). The protein lystes were resolved in a 15% SDS-polyacrylamide gel, and transferred to PVDF membrane. The membrane was washed with TBST buffer (0.1% Tween 20, 150 mM NaCl, 25 mM TrisCl, pH 7.5), blocked for 2 h with a solution containing 5% (w/v) dried nonfat milk in TTBS, and immunoblotted for 2 h with an antibody in a blocking buffer (5% BSA in TTBS). After washing 4 times with TBST with changes every 15 min., the membrane was incubated with HRP-conjugated secondary antibody in TBST (1:5000 dilution) with 5% non-fat milk. The membrane was washed again for 4 times in TBST and visualized by enhanced chemiluminescence.

E. Affinity-purification of Farnesylated Proteins

Farnesylated ras proteins are bound with a specific binding bead in acetonitrile (Farnesylated ras proteins:bead =1:1) and incubated in shaking incubator at room temperature for 1 hr. The products are spun down, and the pellet washed 4 times with 50 mM Tris-Cl, pH 7.6. After washing the farnesylated ras proteins, the pellet is collected and suspended with 20 μl of 1M $K_3PO_4$ pH 12.6 and finally incubated in shaking incubator at room temperature for 1 hr. The supernatant is collected for measurement of Mass spectrometry.

F. Protein In-gel Digestion

The proteins separated in SDS-PAGE gels are visualized by colloidal Coomassie Blue staining method. The bands of interest are in-gel digested by modification of prior methods as follows. Briefly, the protein band is destained in 1 ml of water/methanol solution (50:50, v/v) containing 25 mM $NH_4HCO_3$ (pH 8.0) for three times with solvent change every 10 min. The destained gel band is added with 1 ml of fixation solution (acetic acid:methanol:water, 10:40:50, v/v/v) and vortexed for 3 hrs with the solution change every one hour. The gel is then washed with water twice, 20 min of each time. Transfer gel slices into a new 0.5 mL microcentrifuge tubes and gels are soaked in 100% ACN to dehydrate the gels until they became opaque white. Remove the ACN and dry the gels in Speed-Vac for 20~30 min. The resulting dried gel is rehydrated with adequate amount of ~10 μl of trypsin digestion solution (10 ng trypsin per μL in 50 mM $NH_4HCO_3$, pH 8.0) to completely wet entire gel. Add additional Trypsin solution if necessary. The digestion is carried out at 37° C. overnight. To extract the digested peptides, soak gels in 40 μL 50% ACN/5% TFA for 60 min with vortex and the solution is carefully removed with a gel-loading pipette tip. Extract gels again with another 40 μL aliquot of 75% ACN/0.1% TFA for 60 min. The extracted peptides are pooled and dried with vacuum centrifuge.

G. Protein Identification by Capillary HPLC/Mass Spectrometry

The dried peptide sample is dissolved in 6 μl of HPLC buffer A solution (water:acetonitrile:acetic acid, 97.9:2.0:0.1 (v/v/v)) for mass analysis. HPLC-MS/MS analysis is performed in a LCQ Deca XP (ThermoFinnigan, Palo Alto, Calif.) coupled on-line with a HPLC system (Agilent 1100 Capillary Pump, Agilent Technologies, San Jose, Calif.) and nanospray source. Two microliters of protein digests obtained above is loaded on the HPLC connected with an in-house packed C18 column (~5 cm length, 75 μm ID). The peptides are sequentially eluted from the HPLC column with a gradient of 5%–90% of buffer B (acetonitrile:water:acetic acid, 90:9.9:0.1) in buffer A. The LCQ is operated in a data-dependent mode where the machine measured intensity of all peptide ions in the mass range 400 to 1200 (mass-to-charge ratios) and isolated the two most abundant peptide peaks for collision-induced dissociation using a collision energy level of 35%. The resulting spectra are searched for protein candidates in NCBI non-redundant protein sequence database with the program MASCOT search engine (Matrix Science LTD, London, UK).

Example 8

Synthesis of a Phosphine Capture Reagent and its Biotinylated Derivative

A first generation biotinylated phosphine capture reagent was constructed as outlined in Scheme 2. Diazotization of commercial 17 and iodination of the resultant diazonium salt led to iodide 18. Subsequent cross-coupling of 18 with diphenylphosphine mediated by palladium acetate smoothly evolved differentially derivatized terephthalate mono-ester 19. Then the 19 was linked with a commercial (Pierce: EZ-link™ PEO-LC-amine) water-soluble biotin analog 20 at its amino terminus to furnish 21.

conditions and can be orthogonally, i.e., selectively, cleaved without damage to sensitive macromolecules. A α-methyl-6-nitroveratryl-based photolabile linker was selected for initial evaluation because the two oxygen substituents facilitate (Rinnova, 2000) the nitro-mediated photolytic cleavage with >350 nm UV light which is less harmful to proteins than short wavelength uv light. Also, the α-methyl substituent on the benzylic carbon significantly accelerates the cleavage rate even in aqueous media (Rinnova, 2000). The synthesis, outlined in Scheme 3, closely follows literature precedent (Holmes, 1997). Commercial ketone 20 is converted to oxime 21 by homologation with methyl 4-bromobutyrate followed by condensation with hydroxylamine.

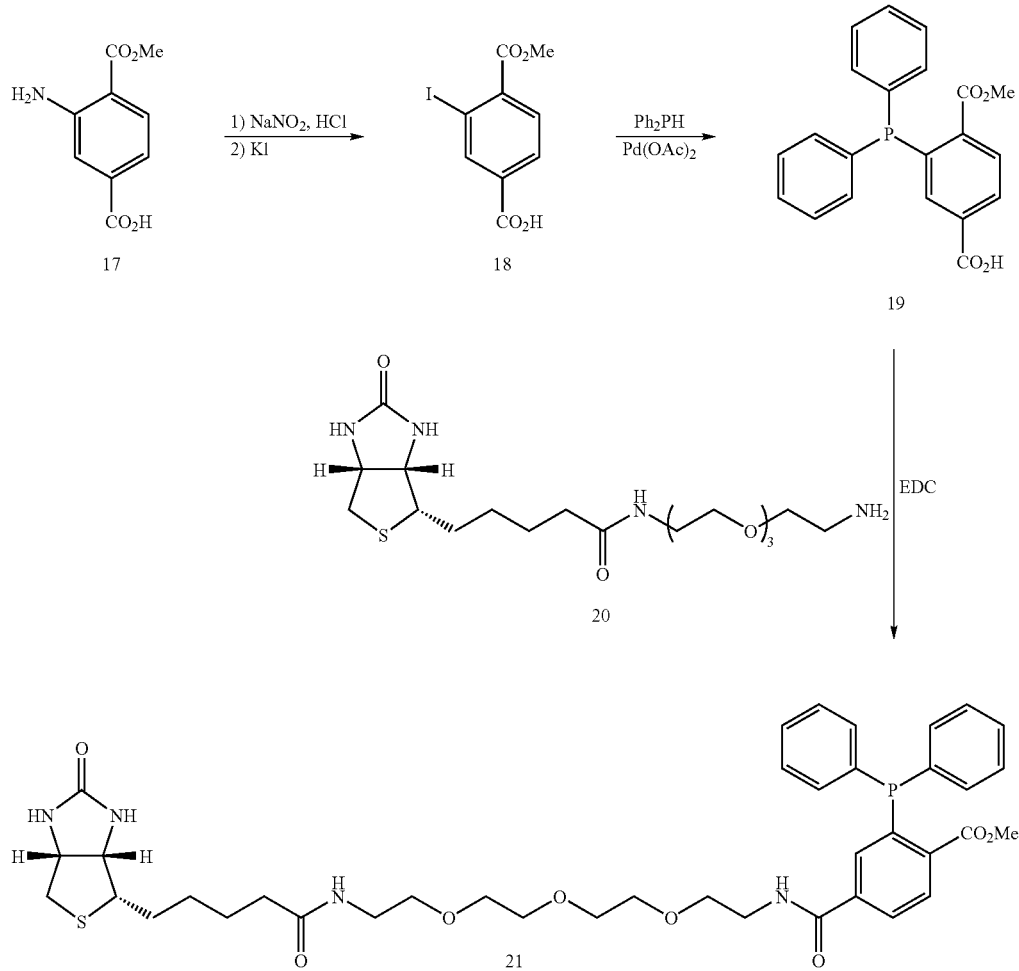

Example 9

Synthesis of Phosphine Capture Reagents with Photolabile Linkers

In some instances, a phosphine capture reagent will be anchored to an insoluble support or other material from which it can be cleaved after conjugation with the organic azide. The introduction of a photolabile linkage is an attractive option since they are generally stable to most reaction Longer, shorter, or more hydrophilic appendages can be substituted for butyrate as desired. Catalytic hydrogenation of the oxime generates a secondary amine that is protected with trifluoroacetic anhydride. Sequential nitration of the resultant amide 22, concomitant saponification of the N-trifluoroacetamide and methyl ester, and dicyclohexylcarbodiimide (DCC) condensation with 19 and further dicyclohexylcarbodiimide (DCC) condensation with water soluble amine and deprotection of tert-butyl group completes the preparation of 23.

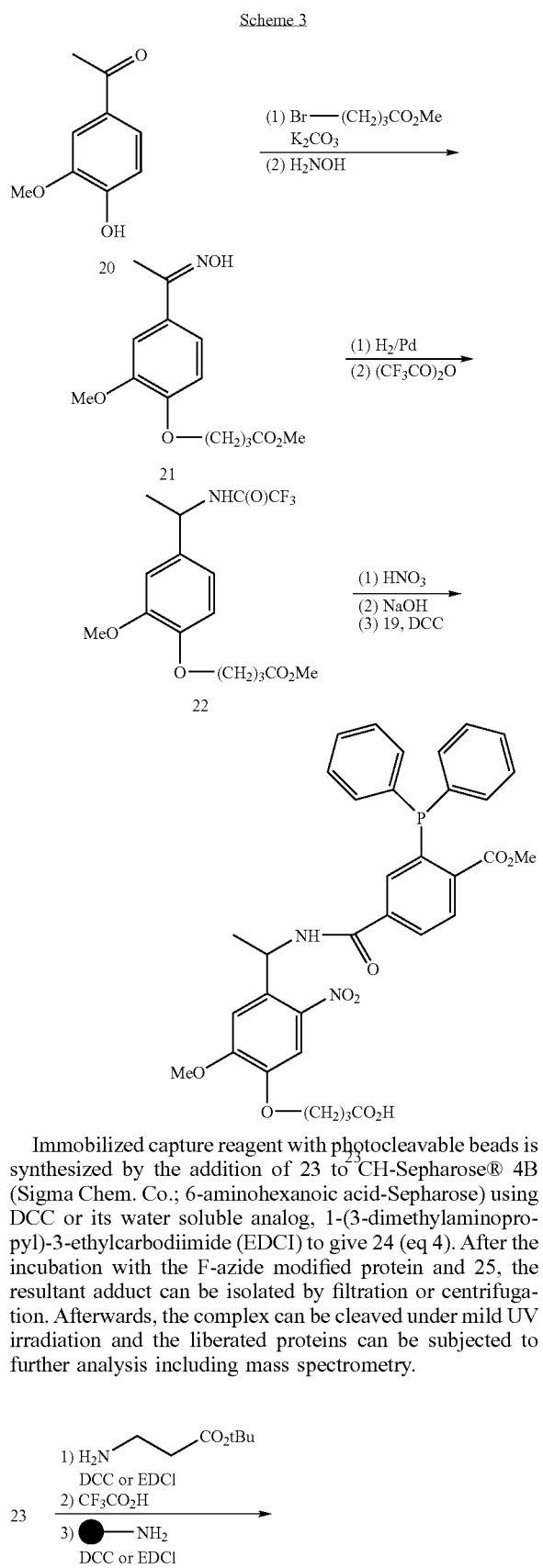

Scheme 3

The stability of 25 towards hydrolysis in aqueous buffers (normal and denaturing), and their reactivity with azide leading to stable amide adducts and photocleavable efficiency will be followed and quantified by HPLC. Products will be characterized by 1H/13C/35P NMR, infrared, and FAB mass spectroscopy. A judicious selection of alcohol leaving group should increase the reactivity of the ester, but still retain the stability to spontaneous hydrolysis during the time frame of the conjugation reaction with the azido-moiety.

Immobilized capture reagent with photocleavable beads is synthesized by the addition of 23 to CH-Sepharose® 4B (Sigma Chem. Co.; 6-aminohexanoic acid-Sepharose) using DCC or its water soluble analog, 1-(3-dimethylaminopropyl)-3-ethylcarbodiimide (EDCI) to give 24 (eq 4). After the incubation with the F-azide modified protein and 25, the resultant adduct can be isolated by filtration or centrifugation. Afterwards, the complex can be cleaved under mild UV irradiation and the liberated proteins can be subjected to further analysis including mass spectrometry.

Example 10

Synthesis and Evaluation of GG-azide-OH and GG-azide-PP Analogues

Geranylgeranyl pyrophosphate azides 34a, 34b and 34c can efficiently be synthesized as summarized in Scheme 4. Similarly like farnesyl pyrophosphate azides 16a, 16b and 16c as described in Scheme 1, commercial geranylgeranyl acetate 25 can be converted to geranylgeranyl pyrophosphate azides 34a, 34b and 34c in good yield.

-continued

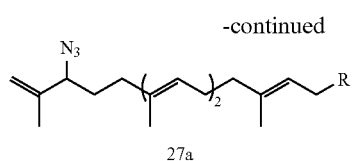

27a

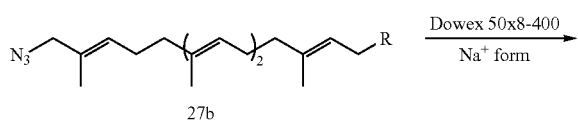

27b

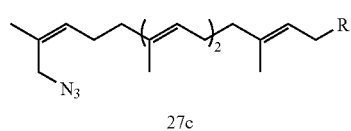

27c

K₂CO₃ — 27a, 27b, 27c: R = OAc
NCS — 28a, 28b, 28c: R = OH
— 29a, 29b, 29c: R = Cl
(Bu₄N)₃HP₂O₇ — 30a, 30b, 30c: R = O₇P₂(NBu₄)₃
Dowex 50x8,
NH₄⁺ form — 31a, 31b, 31c: R = O₇P₂(NH₄)₃

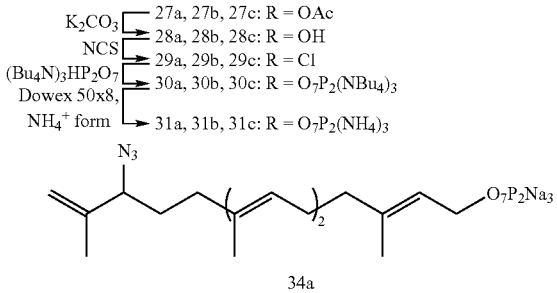

34a

34b

+

34c

Labeling efficiency of geranylgeranylation substrates, GG-azide-OH and GG-azide-PP, is evaluated by Western blotting analysis of protein lysates using HRP-conjugated streptavidin as described herein for F-azide-modified proteins.

REFERENCES

The following references, to the extent that they provide exemplary procedural or other details supplementary to those set forth herein, are specifically incorporated herein by reference.

Adjei et al., *Clinical Cancer Res.*, 6:2318–2325, 2000.
Aebersold and Mansion, *Nature*, 422:198–207, 2003.
Baron et al., *Proc. Natl. Acad. Sci. USA*, 97:11626–11631, 2000.
Chi et al., *Science*, 301:964–967, 2003.
Davisson et al., *Methods Enzymol.*, 110:130–44, 1985.
End et al., *Cancer Res.*, 61:131–137, 2001.
Fu and Casey, *Recent Prog. Horm. Res.*, 54:315–342, 1999.
Gibbs et al., *J. Med. Chem.*, 42:3800–3808, 1999.
Gololobov and Kasukhin, *Tetrahedron*, 48:1353–1406, 1992.
Gygi et al., *Nat. Biotechnol.*, 17:994–999, 1999.
Hanash, Nature, 422:226–232, 2003.
Holmes, *J. Org. Chem.*, 62:2370–2380, 1997.
James et al., *J. Biol. Chem.*, 269:27705–27714, 1994.
Kiick et al., *Proc. Natl. Acad. Sci. USA*, 99:19–24, 2002.
Kim et al., *Mol. Cell Biol.*, 10:5945–5949, 1990.
Lin et al., *J. Gen. Virol.*, 80:91–96, 1999.
McGuire and Sebti, *Oncogene*, 14:305–312, 1997.
Melkonian et al., *J. Biol. Chem.*, 274:3910–3917, 1999.
Moores et al., *J. Biol. Chem.*, 266:14603–14610, 1991.
Reiss et al., *Cell*, 62:81–88, 1990.
Rinnova et al., *J. Pept. Sci.*, 6:355–365, 2000.
Saxon et al., *J. Am. Chem. Soc.*, 124:14893–14902, 2002.
Seabra et al., *Cell*, 65:429–434, 1991.
Sinensky et al., *J. Biol. Chem.*, 265:19937–19941, 1990.
Staros et al., *Biochem. Biophys. Res. Commun.*, 80:568–572, 1978.
Tamanoi et al., *Cell Mol. Life Sci.*, 58:1636–1649, 2001a.
Tamanoi et al., *J. Cell Biochem.*, 64–70, 2001b.
Wu et al., *Nat. Biotechnol.*, 21:532–538, 2003.
Yokoyama et al., *Proc. Natl. Acad. Sci. USA*, 88:5302–5306, 1991.
Zoretic et al., *J. Org Chem.*, 61(5):1806–1813, 1996.

What is claimed is:

1. A method for detecting at least a first isoprenylated protein in a cell comprising:
   a) obtaining a substrate of at least a first protein in said cell, wherein the substrate is a synthetic isoprenyl azide substrate comprising at least a first azide;
   b) contacting the cell with the synthetic isoprenyl azide substrate under conditions wherein the cell takes up synthetic isoprenyl azide substrate and the synthetic isoprenyl azide substrate reacts with the first protein to produce at least a first isoprenylated protein; and
   c) detecting at least said first isoprenylated protein from proteins produced by said cell by contacting the proteins produced by said cell with a phosphine capture reagent, wherein capture occurs by the Staudinger reaction.

2. The method of claim 1, wherein the first protein is farnesylated.

3. The method of claim 1, wherein detecting comprises isolating the first protein.

4. The method of claim 2, wherein farnesyl pyrophosphate (FPP) is inhibited in said cell.

5. The method of claim 4, wherein FPP is inhibited by contacting the cell with an HMG Co-A reductase inhibitor.

6. The method of claim 4, wherein FPP is inhibited by contacting the cell with lovastatin.

7. The method of claim 1, wherein the isoprenyl azide is further defined as an azido prenyl diphosphate.

8. The method of claim 1, wherein the isoprenyl azide is further defined as an azido farnesyl diphosphate.

9. The method of claim 1, wherein the first protein is native to said cell.

10. The method of claim 1, wherein the step of detecting comprises Western blot analysis.

11. The method of claim 1, wherein the phosphine capture reagent is bound to a solid Support.

12. The method of claim 11, wherein the phosphine capture reagent is bound to a solid support with a photocleavable linker.

13. The method of claim 1, wherein the phosphine capture reagent comprises a label.

14. The method of claim 13, wherein the label comprises a fluorescent, colorimetric, chemiluminescent, or radioactive label.

15. The method of claim 13, wherein the label comprises an antigen.

16. The method of claim 15, wherein the antigen is biotin.

17. The method of claim 16, wherein detecting in step c) comprises affinity-purification with streptavidin- and/or avidin-conjugated beads.

18. The method of claim 11, wherein the solid support comprises a bead composed of silica gel, polystyrene, starch, sugars, or organic or inorganic matrixes.

19. The method of claim 1, wherein a nucleophile in said Staudinger reaction is immobilized on a polymer.

20. The method of claim 19, wherein the polymer is selected from the group consisting of: mono-methyl polyethylene oxide, SEPHAROSE, TENTAGEL, AGROGEL-Wang, polysaccharide, polystyrene, polyethane, and co-polymers thereof.

21. The method of claim 1, wherein the synthetic prenyl azide substrate is a substrate for a plurality of proteins and wherein the step of detecting comprises detecting the plurality of proteins.

22. The method of claim 1, wherein the first protein is Ras.

23. The method of claim 1, wherein the synthetic isoprenyl azide substrate has the molecular formula:

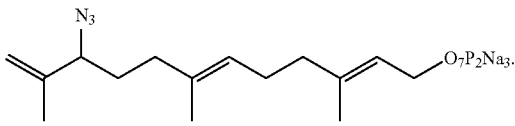

24. The method of claim 1, wherein the synthetic isoprenyl azide substrate has the molecular formula:

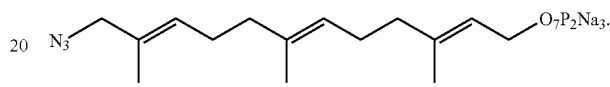

25. The method of claim 1, wherein the synthetic isoprenyl azide substrate has the molecular formula:

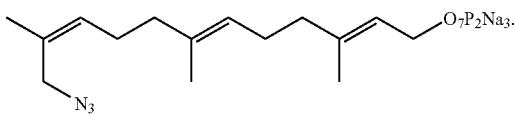

26. A method for labeling a protein in a cell, comprising:
   a) preparing a synthetic substrate of said protein by incorporating at least a first azide in a molecule, wherein the synthetic substrate has molecular formula selected from the group consisting:

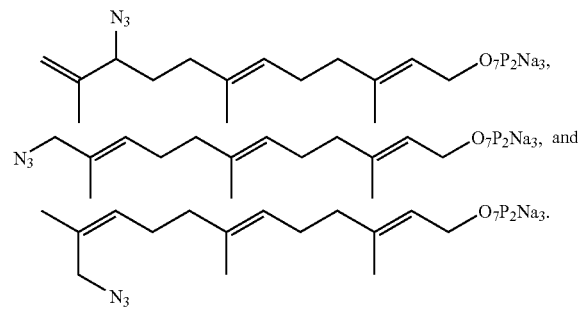

b) contacting the cell with the synthetic substrate under conditions wherein the synthetic substrate is taken up and incorporated into the protein, wherein the protein is labeled with said first azide.

27. The method of claim 26, wherein the protein is prenylated.

* * * * *

UNITED STATES PATENT AND TRADEMARK OFFICE
CERTIFICATE OF CORRECTION

PATENT NO. : 7,070,941 B2  Page 1 of 1
APPLICATION NO. : 10/715329
DATED : July 4, 2006
INVENTOR(S) : Zhao et al.

It is certified that error appears in the above-identified patent and that said Letters Patent is hereby corrected as shown below:

In claim 1, column 21, line 8, after "takes up", insert --the--therefor.

In claim 11, column 21, line 36, delete "Support" and insert --support-- therefor.

In claim 26, column 22, line 39, after "has " insert --a -- therefor.

Signed and Sealed this

Nineteenth Day of December, 2006

JON W. DUDAS
*Director of the United States Patent and Trademark Office*

UNITED STATES PATENT AND TRADEMARK OFFICE
CERTIFICATE OF CORRECTION

PATENT NO. : 7,070,941 B2
APPLICATION NO. : 10/715329
DATED : July 4, 2006
INVENTOR(S) : Zhao et al.

It is certified that error appears in the above-identified patent and that said Letters Patent is hereby corrected as shown below:

In claim 1, column 21, line 8, after "takes up", insert --the--therefor.

In claim 11, column 21, line 36, delete "Support" and insert --support-- therefor.

In claim 26, column 22, line 39, after "has " insert --a -- therefor.

Signed and Sealed this

Ninth Day of January, 2007

JON W. DUDAS
*Director of the United States Patent and Trademark Office*

SEQUENCE LISTING

<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 1

Lys Lys Phe Phe Cys Ala Ile Ser
 1               5